United States Patent [19]
Iwasyk et al.

[11] Patent Number: 5,811,496
[45] Date of Patent: Sep. 22, 1998

[54] PROCESS FOR POLYMERIZATION OF POLYESTER OLIGOMERS

[75] Inventors: John Maurice Iwasyk, Wilmington; Julie Anderson Rakestraw, Newark, both of Del.; Kenneth Wayne Leffew, Kennett Square, Pa.

[73] Assignee: E.I. du Pont de Nemours and Company, Wilmington, Del.

[21] Appl. No.: 576,657

[22] Filed: Dec. 21, 1995

[51] Int. Cl.⁶ ................................................. C08F 20/00
[52] U.S. Cl. ..................... 525/444; 528/272; 528/279; 528/283; 528/285; 528/298; 528/308.6; 528/491; 528/492; 528/503; 525/437; 525/444
[58] Field of Search ....................... 528/272, 279, 528/283, 285, 298, 308.6, 491, 492, 503; 525/437, 444

[56] References Cited

U.S. PATENT DOCUMENTS 3,480,587 11/1969 Porter ......................................... 526/64
3,496,146 2/1970 Mellichamp, Jr. .................... 528/308.3
3,590,072 6/1971 Leybourne, III ........................... 560/94
4,212,963 7/1980 Lehr et al. ................................. 528/272

FOREIGN PATENT DOCUMENTS 0 240 279  10/1987  European Pat. Off. ........ C07C 67/08
A 2 452 503  10/1980  France .

*Primary Examiner*—Sammuel A. Acquah

[57] ABSTRACT

This invention is directed to an improved process for producing a polyester oligomer. The process employs a pipeline reactor, having at least two stages, in which the degree of polymerization of an oligomeric feed material is raised from about 2–10 to about 2–40 and the ratio of carboxyl to hydroxyl end groups in the product is reduced. In a first stage of the process, a monomeric diol or polyol, such as ethylene glycol, is added to a melt of the oligomeric feed material. In a second stage of the process, the molecular weight of the oligomer is increased by removal of volatile reaction by-products, including water and polyol. The oligomer produced by the present invention may be used in making higher molecular weight polyesters.

19 Claims, 2 Drawing Sheets

PROCESS FOR POLYMERIZATION OF POLYESTER OLIGOMERS

FIELD OF THE INVENTION

This invention is directed to an improved process for the polymerization of polyester oligomers produced from dicarboxylic acids, such as terephthalic acid (TPA), or their esters. More particularly, the invention involves polymerizing the oligomer in a pipeline reactor having at least two stages, to obtain an ends-balanced oligomer having a degree of polymerization of 2 to 40. Such oligomers are useful in an overall process for making higher molecular weight polyesters.

TECHNICAL BACKGROUND

Polyester production from diacids or their esters and polyols or glycols, for example, from dimethyl terephthalate (DMT) and ethylene glycol, is well known. This has usually been accomplished by stage-wise melt polymerization under vacuum conditions. In order for such methods of polymerization to achieve commercially acceptable levels, the condensation by-products, for example, ethylene glycol, need to be removed from the reaction system. Typically, the by-products and excess glycol are vaporized, usually under vacuum conditions, and end up as a waste-water stream. Subsequently, the waste-water stream requires treatment and may contribute volatile organic emissions to the air. Moreover, the presence of excess ethylene glycol in the polymerization reactor may have a deleterious effect on the physical properties of the product.

The prior art discloses the difficulties encountered in attempting the direct esterification of an insoluble dicarboxylic acid and a polyol. U.S. Pat. No. 3,590,072 and British patent 1,154,538 discuss the plugging of feed lines by agglomeration of the acid/alcohol slurry as well as heat transfer problems.

A single stage reaction process is described in U.S. Pat. No. 3,480,587. The reference describes preparation of a fiber or film-forming polyester or copolyester where at least part of the polycondensation takes place while the liquid reaction mixture flows along a long, narrow tube in turbannular flow. The movement of the liquid along the tube is cocurrent with the flow of a gaseous fluid which is chemically inert to the liquid reaction mixture. The rate of flow of the gaseous fluid is such that during at least part of the residence time the partial pressure of glycol in the gaseous fluid is below the equilibrium partial pressure for the reaction mixture. The ratio of the sectional area of the tube divided by the length of the wetted perimeter should preferably be less than 2.5 cm. In one embodiment of the process described in the patent, the reaction mixture entering the tube is of average degree of polymerization 27 and the product issuing from the tube is of Viscosity Ratio between 1.7 and 2.0 in 1% solution orthochlorophenol at 25° C. (e.g., of degree of polymerization of 65 to 100 units).

An atmospheric-pressure process for the continuous production of polyester is disclosed in commonly assigned patent application, U.S. Ser. No. 08/138312 (by Bhatia). In the latter application, a melt of dihydroxy ethylene terephthalate, or its low molecular weight oligomer, obtained by esterifying terephthalic acid or transesterifying dimethyl terephthalate with ethylene glycol, is intimately contacted with an inert gas which flows countercurrent to the melt, in order to facilitate polymerization and removal of the volatile reaction by-products.

Because of the problems described above, it would be desirable to reduce the problem of excess ethylene glycol in the production of polyester oligomers and, at the same time, to efficiently and economically obtain the desired oligomer in terms of degree of polymerization and ends balance. By the term "ends balance" is meant the ratio of the carboxyl to the hydroxy functional groups in the oligomer product.

SUMMARY OF THE INVENTION

The process of the present invention comprises a multi-stage pipeline reactor, having at least two stages, for polymerization of a polyester oligomer in which the carboxy/hydroxy ends balance is decreased and the degree of polymerization (DP) of an oligomer may also be raised, from an initial DP of about 2 to 10 to a product DP, at the end of the process, of about 2 to 40. More specifically, the process of this invention involves a process for preparing a prepolymer in a pipeline reactor having at least two stages, which process comprises:

(a) in a first stage of the reaction process, in a pipeline reactor, optionally in the presence of a polyester polymerization catalyst, mixing and contacting a polyol monomer with an oligomer feed material in melt form, wherein the oligomer feed material has a degree of polymerization (DP) of 2 to about 10 and is the reaction product of a mixture of monomers comprising a dicarboxylic acid or its ester and the polyol, and wherein the polyol monomer to acid ratio of the reaction mixture is about 1.01:1 to about 1.5:1, and wherein the reaction mixture is within a predetermined temperature and pressure range;

(b) in a second stage of the reaction process, in a pipeline reactor, removing volatile reaction by-products, including water and excess polyol monomer, from the melt, under reduced pressure, by the presence of an flowing inert gas, thereby increasing the molecular weight of the product exiting the first stage of the reaction process.

The present invention allows for the substantial reduction of the ratio of a polyol monomer, such as ethylene glycol, to a diacid, such as terephthalic acid, thereby reducing the quantity of excess polyol monomer. The invention described herein also avoids the problems of slurry handling in the pipeline by beginning with an oligomer formed in a separate direct esterification step, such as described in U.S. Pat. No. 3,496,146, which describes the formation of low molecular weight oligomer by direct esterification of terephthalic acid and a glycol. Instead, the method disclosed in U.S. Pat. No. 3,496,146, hereby incorporated by reference in its entirety, can be employed to produce the feed material for the present invention.

The present invention maximizes the utility of the pipeline reactor by beginning with feed material of a low molecular weight oligomer, thus avoiding handling of the acid/alcohol slurry, as well as avoiding excessive melt polymerization prior to the introduction of the feed to the pipeline reactor. The material is discharged from the pipeline reactor prior to reaching viscosities high enough to inhibit flow of the polyester.

The present invention employs an inert gas such as nitrogen, under positive pressure, thereby eliminating or reducing the problems of leakage of air into the system, which can cause degradation reactions and the development of color in traditional vacuum polymerization systems. Also, the present process has the advantage of eliminating or reducing the need for wastewater handling, vacuum jets, and emissions problems, without requiring expensive and sometimes unreliable vacuum pump systems.

DETAILED DESCRIPTION OF THE INVENTION

Figure 1:
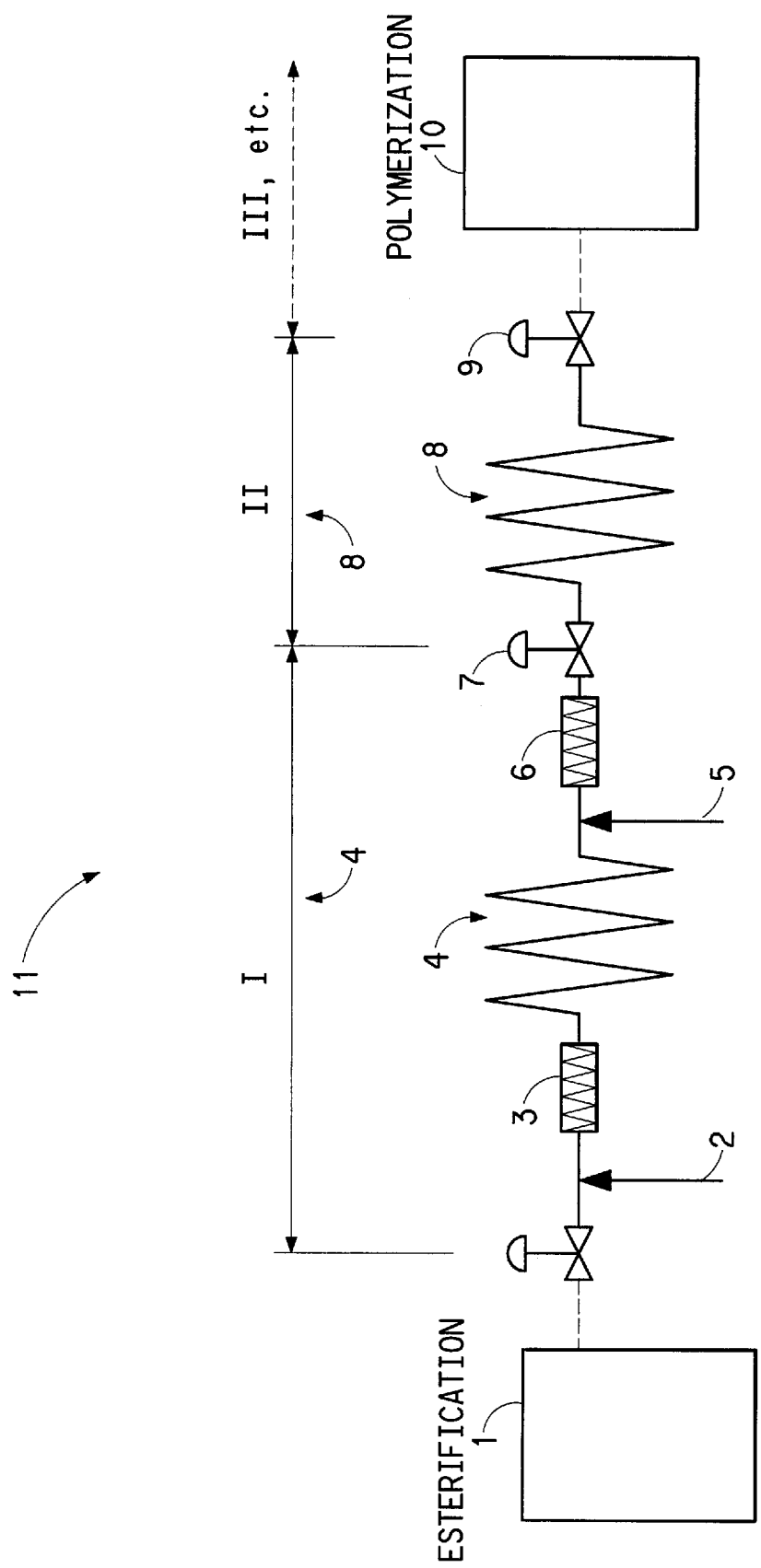
FIG. 1 is a schematic drawing of one embodiment of the present process employing a multi-stage pipeline reactor, as may be practiced on a commercial scale.

As indicated above, this invention is directed to an improved process and apparatus for the polymerization of polyester produced from dicarboxylic acids or their esters, such as terephthalic acid (TPA). The process employs a pipeline reactor having at least two stages. The process polymerizes an oligomeric feed material having a degree of polymerization of 2–10 and typically produces an oligomeric product having a degree of polymerization of 2–40, preferably 5–35, most preferably 8 to 30. In the first stage of the present process, a polyol, such as ethylene glycol, is added to the oligomeric feed material, a low molecular weight polyester oligomer prepolymer melt, wherein the mole ratio of polyol to acid allows for the desired ends-balancing which enables the production of high molecular weight polyester during subsequent processing. The polyol to acid ratio of the reaction mixture is suitably about 1.01:1 to about 1.5:1, preferably about 1.1:1 to about 1.4:1, most preferably 1.15:1 to 1.3:1. In a second or later stage, the molecular weight of the prepolymer is increased by removal of volatile reaction by-products, including water and polyol from the melt.

The carboxyl/hydoxyl ends balance of the the oligomeric feed material is typically 1:1 to 1:0.25 (one:one to one:one-fourth) and the carboxy/hydoxyl ends balance of the oligomeric product is suitably 1:2 to 1:8.

In the first stage of the reaction process, a polyol or diol, such as ethylene glycol, is added to a low molecular weight polyester oligomer melt in a mole ratio of the polyol to acid that allows for ends-balancing and enables the production of a high molecular weight polyester during subsequent processing. The oligomer is sometimes also referred to as a prepolymer with respect to the high molecular weight polyester.

Accordingly, a polyester oligomer, of low molecular weight, in melt form, is fed to the entrance of a pipeline reactor. By using low molecular weight polyester oligomer which has been previously esterified, handling problems, recognized in the prior art and commonly encountered with feeding slurries of glycol and terephthalic acid or the like, are eliminated.

The first stage is operated within a range between 20 psig and 300 psig. Operation above the vapor pressure may be employed to avoid the polyol flashing and then rapidly flowing downstream, which could lead to major inefficiencies. Higher pressure may also be employed to obtain efficient mixing for ends balancing, and to reduce the volume and costs of the reactor by maintaining a high liquid phase fraction ratio, and, finally, to reduce the amount of polyol loss. On the other hand, lower vapor pressures may be more economical due to lower capital and operating costs for nitrogen injection in the case wherein nitrogen is injected at the end of the first stage of the reactor, as preferred. If operating below the vapor pressure of the glycol, however, mixing of the glycol vapor and the oligomer melt should be carried out such that the glycol is incorporated into the melt and is not carried away in the gas phase before reacting. Several methods for achieving this degree of mixing are possible, including the use of a static mixer followed by vertical flow through a coiled reactor section.

The residence time in the first stage is preferably sufficient to drive the esterification reaction to equilibrium, or to have the esterification reaction approach equilibrium. Otherwise, an excess amount of polyol may be lost due to flashing in the subsequent lower pressure second stage. Thus, the process is preferably designed to operate as close to equilibrium as possible. The residence time for both the first and second stage is preferably designed for the maximum throughput at minimum reactor temperature conditions so that the product composition will be relatively constant with turndown ratio and any temperature changes. However, the skilled artisan will appreciate that practical limitations to the turndown ratio and reaction temperature must be considered to avoid designing an oversize reactor which will provide excessive residence times which would lead to degradation under standard operating conditions.

The process temperature should be above the melting point of the oligomer in the reaction mixture, and should be sufficiently high so that reactor holdup time is not excessive. However, the temperature should not be so high that undesirable side reactions are excessive. Each stage of the pipeline reactor can be operated at different temperatures or at the same temperature in a common shell to minimize costs.

The first and second stages may contain mixers, preferably static mixers. Preferably there is an initial mixer in the first stage which is the primary mixing device for contacting the polyol with the oligomer reactant. Additionally, there may be static mixers placed in the first stage to recontact any gas phase polyol with oligomer reactant, in order to improve the first stage yield.

In a second stage of the reaction process, in the pipeline reactor, and usually in any other subsequent polymerization stages, the molecular weight of the prepolymer is increased, ultimately to the desired level, by the removal of volatile reaction by-products, including water and the polyol, for example glycol, from the melt.

As indicated above, an inert gas is employed to drive the reaction in the second stage. The inert gas is preferably introduced at the end of the first stage to allow intimate mixing and possible dissolution in the oligomer phase. This has the advantage that the mixture of inert gas and oligomer upon pressure letdown will foam and froth, but not excessively, such that a greater amount of interfacial area will be generated, which is beneficial for the condensation reaction which is to take place in the second stage.

There will be a pressure drop in the second stage which is of sufficient magnitude that it will reduce or eliminate the desirabilty of a vacuum operation. Vacuum operation is less preferred because it may increase the potential for entrainment losses through the separator stack and for reasons disclosed earlier herein.

Additives and catalysts may optionally be injected and mixed either in the first or second stage, or both.

By decreasing the mole ratio of polyol to acid, the amount of polyol that must be removed during polymerization is decreased, thus reducing the amount of waste polyol generated. Further, the tendency to form polyol linkages, such as diethylene glycol, which can have a deleterious effect on the physical properties of the polymer (e.g., on crystallization rate, dyeability, etc.), is also reduced.

With reference to FIG. 1, a preferred embodiment of the present invention is shown, including a pipeline reactor generally shown at 11, which reactor is divided into two stages I and II. By the term "pipeline reactor" is typically meant an axially elongated substantially cylindricallyshaped apparatus, although shapes may vary if not detrimental to the purpose of this invention. The terms "first stage" and "second stage" are not meant to exclude additional stages at any point within the reaction process or along the pipeline reactor.

Referring again to FIG. 1, a dicarboxylic acid or its ester, such as terephthalic acid (TPA), is reacted with a polyol (usually a diol), such as ethylene glycol, by means of a melt-phase direct esterification process in an esterifier 1. The esterification produces a low molecular weight oligomer of average degree of polymerization of 2 to about 10, preferably about 5 to about 10. In the case where terephthalic acid and ethylene glycol are reacted in the direct esterification process, the oligomer produced typically has an intrinsic viscosity (IV) of 0.09 to 0.16 dl/gm, and carboxyl ends of 600 to 1200 Eq/$10^6$ gms.

The carboxyl ends of the oligomer feed material produced in the esterifier 1 are subsequently reduced in the present process by means of the pipeline reactor. Although typically the DP also increases by the end of this process, this may not necessarily be the case. For example, although the DP of the reaction mixture will be increased in the second stage of the process, the DP will actually decrease, in some cases to a greater extent, in the first stage of the reactor.

In the embodiment shown in FIG. 1, additional diol is injected at injection point 2 to provide sufficient diol for formation of a prepolymer with a mole ratio and ratio of carboxyl/hydroxyl ends appropriate to allow production of high molecular weight polymer in subsequent processing steps. Optionally, a catalyst and/or other additives, such as delusterants, may be added with the diol. The diol and molten oligomer flow through a static mixer section 3 to provide for improved mixing and reactant contact. The mixture flows into a section or zone 4 of the pipeline reactor, which zone operates under pressure and provides sufficient residence time to allow for reaction.

In the second stage of the process, generally designated as II, the pipeline reactor operates at a lower pressure than in the first stage and functions to increase the molecular weight of the polymer melt. An inert gas may be injected at injection point 5, preferably just before the end of the first stage of the reactor. It is preferable to inject the inert gas at that location, rather than at the beginning of the second stage, to increase mixing of the inert gas with the reaction mixture. The mixture of melt and inert gas flow cocurrently, optionally through static mixer 6, to provide improved mixing and reactant contact. The mixture passes through a letdown valve 7 or other device to reduce the pressure to second stage II which operates at substantially atmospheric pressure, with the polycondensation reaction driven by the reduction in partial pressure of the gas and diol provided by injection of the inert gas. Optionally, to some extent, vacuum may also be applied in stage II. Preferably, however, the use of vacuum is not necessary.

The reaction mixture then passes into pipeline reactor section 8 and produces prepolymer having an average degree of polymerization of 2 to 40, preferably about 5 to 35, more preferably about 10 to 25. Such prepolymer is suitable for subsequent processing to form high molecular weight polymer. Prepolymer exits the pipeline reactor at 9 and may be fed to a subsequent polymerization reactor, generally indicated as 10 in FIG. 1, with or without intermediate processing before, for example, solid-state polymerization, wherein the prepolymer may first be formed into semi-crystalline pellets and/or subjected to further melt polymerization.

As indicated above, the pipeline reaction process as described herein is not necessarily limited to two stages. It is within the scope of this invention to process the oligomer in multiple stages of a pipeline reactor. For example, an additional stage III, prior to polymerization reactor 10, is referenced on FIG. 1. Any additional stages would be provided with the desired or proper pressure conditions of inert gas addition or optional vacuum as required.

Figure 2:
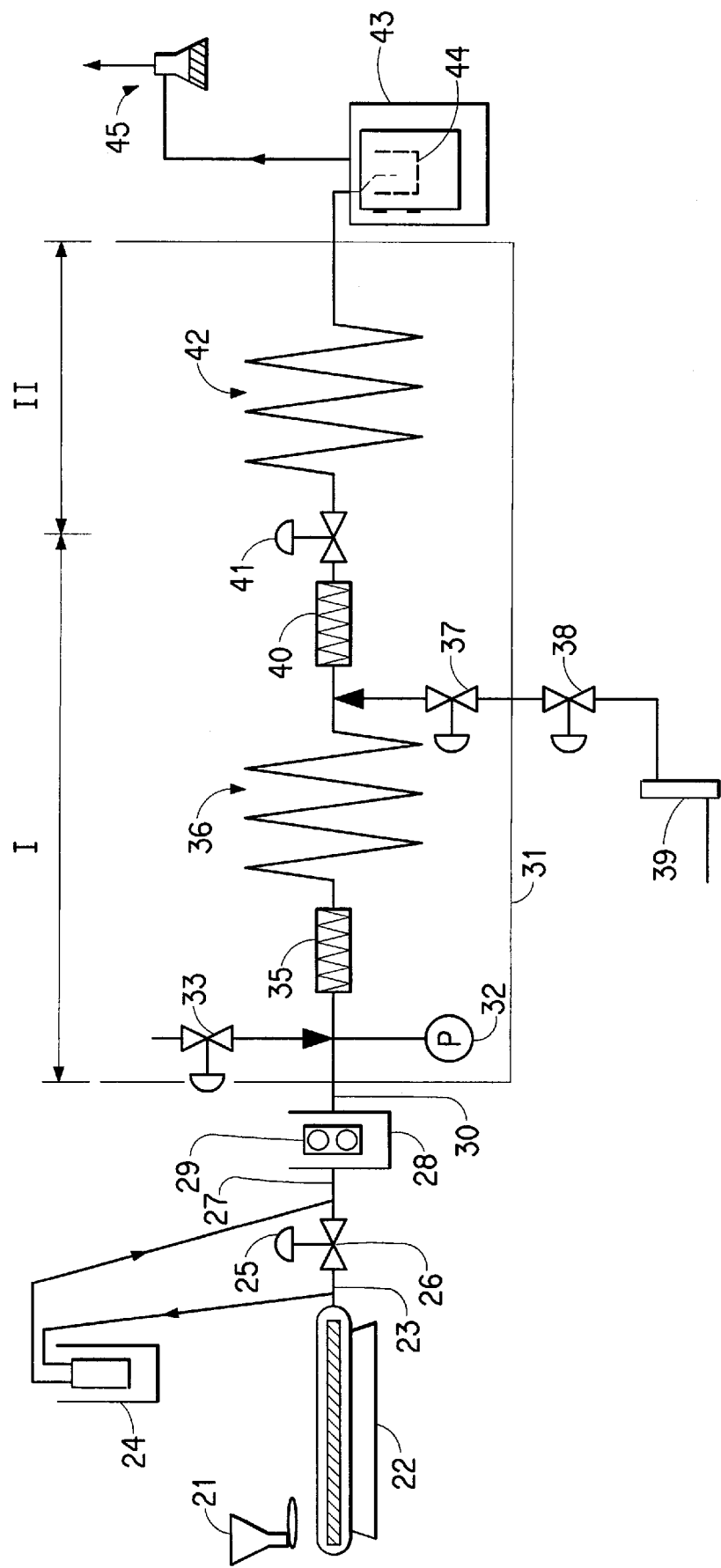
FIG. 2 is a schematic drawing of one embodiment of the present invention employing a multi-stage pipeline reactor as used to produce a polyester oligomer in smaller quantities.

The present invention will now be described with reference to a demonstration on a smaller scale, such as employed in the following examples. For this purpose, the oligomer, which was prepared remotely, was solidified and ground into a powder prior to feeding it to a pipeline reactor. Referring now to FIG. 2, the powdered oligomer is loaded into a feeder 21, which may be for example a loss-in-weight feeder model LWF-T20, manufactured by K-Tron Corporation of Pitman, N.J. The powdered oligomer is metered into a melting device 22, such as a 30-mm twin screw extruder manufactured by Werner & Pfleiderer Corporation of Ramsey, N.J. The oligomer is melted and conveyed through the extruder. The molten oligomer exits the extruder through an oil-jacketed, heated transfer line 23. The heated fluid is provided by a heated oil bath 24 with a circulating pump. The heated oil bath may be a high temperature oil bath distributed by Brinkmann Instruments of Westbury, N.Y. and manufactured by Lauda AG of Germany. The heated transfer lines may be heated using circulating heat transfer fluids such as high temperature silicone oil manufactured by Dow-Corning of Midland, Mich., or Marlotherm S dibenzyltoluene heat transfer fluid manufactured by Huls America, Inc. of Piscataway, N.J. Alternatively, electrical heating or other means may be used to provide sufficient heat to maintain the oligomer at its desired temperature above its freezing point.

The molten oligomer flows through a three-way valve 25 and is directed either to the pipeline reactor, or, on startup and shutdown, to waste collection 26. The oligomer stream flows through an oil-traced heated transfer line 27. This transfer line is heated by a circulating oil pump in a second oil bath 28. The heated oil bath may be a model T.C.V. manufactured by Tamson of Holland or similar device. The oligomer stream flows to a metering pump 29 located in a heated oil bath 28. The pump may be a model HPB ¼ capacity melt pump manufactured by Zenith Nichols of Waltham, Mass. The metering pump is used to control the flow of oligomer to the pipeline reactor.

The oligomer flows from the melt through a heat transfer fluid jacketed transfer line 30 into the first stage (I) of the pipeline reactor which is located within a heat transfer fluid filled bath 31. The heated oil bath may be a Lauda-Brinkmann high temperature oil bath as described above. The pressure of the oligomer stream is measured using, for example, a pressure transducer 32 manufactured by Dynisco Instruments of Philadelphia, Pa. Ethylene glycol, optionally mixed with catalyst, is injected into the molten oligomer stream through injection valve 33. Possible catalysts used to aid the esterification reaction include antimony glycolate, such as S-24 manufactured by Elf Atochem North America of Philadelphia, Pa., or $Sb_2O_3$, antimony trioxide, manufactured by Laurel Industries, Inc. of Cleveland, Ohio, or titanium (IV) isopropoxide obtained from Aldrich Chemical Co. of Milwaukee, Wis. The catalysts are previously mixed with ethylene glycol at the desired concentration. A metering pump 34, such as a model 500D syringe pump with Series D controller, manufactured by Isco, Inc. of Lincoln, Nebr., is used to control the flow of the ethylene glycol. After injection, the mixture of oligomer, ethylene glycol, and (optionally) catalyst flows through static mixers 35, such as a Kenics mixer with ¼" OD and 20–25 mixer elements manufactured by Kenics Static Mixers of Chemineer, Inc., of North Andover, Mass., to provide improved mixing between the oligomer and ethylene glycol.

Esterification of the oligomer and glycol occurs in the pipeline reactor section 36, providing ends-balancing by the incorporation of ethylene glycol into the oligomer, thus reducing the number of carboxyl ends and increasing the mole ratio of ethylene glycol/terephthalic acid, to allow the production of high molecular weight polymer in subsequent processing steps.

Nitrogen is injected through an injection valve 37 into the center of the melt stream at the end of the first stage of the pipeline reactor. The purpose of the nitrogen stream is to reduce the partial pressure of the ethylene glycol in the second stage of the pipeline reactor (II) and allow polymerization to proceed as desired. The degree of polymerization upon exit is controlled by varying the nitrogen flow rate using a metering valve 38 and reading the throughput from a rotameter 39, such as a model R-6-15-A obtained from Brooks Instrument Division of Emerson Electric Co. of Hatfield, Pa.

The oligomer and nitrogen may flow through static mixer section 40, comprised, for example, of two SMX mixers with ⅜" OD manufactured by Koch Engineering Company, Inc. of Wichita, Kans. and a 10–15 mixer element with ⅜" OD manufactured by Kenics Static Mixers of Chemineer, Inc., of North Andover, Mass. However, the reaction, as described, has been run successfully both with and without static mixer section 40.

The prepolymer and nitrogen flow through a letdown valve 41 and into a flasher section 42 which may comprise 25 feet of ½" OD stainless steel tubing and which provides residence time for the polycondensation and esterification reactions to proceed as desired.

The two-phase mixture, nitrogen, water and ethylene glycol vapors and prepolymer melt, flows from the pipeline reactor oil bath 31 through a jacketed transfer line to the separator 43. The melt is collected in a quench bath in a sample collection beaker 44. The vapor is removed through an exhaust line to a bank of condensers 45 to remove the ethylene glycol and water from the gas stream. The nitrogen stream then flows through vacuum pumps to remove any residual ethylene glycol prior to discharge through a vent line (not shown). Data on system temperatures and pressures are recorded using a Kaye 4S Plus Digistrip recorder. Process monitoring of selected points is also accomplished using Genesis software version 3.52 on a Texas Microsystems N286 personal computer.

The process of the present invention is generally applicable for use regarding any dihydroxy ester of any dicarboxylic acid, or low molecular weight oligomer thereof. Diol addition, for ends balancing, would be dependent on the oligomer being processed. Often catalyst or other additives are introduced to the system via glycol solution in stage I.

Suitable catalysts for facilitating the polymerization include any one or more polyester polymerization catalysts known in the prior art to catalyze such polymerization processes, such as, but not limited to, compounds of antimony, germanium and titanium. Antimony trioxide ($Sb_2O_3$) is an especially effective catalyst which may be introduced, for convenience, as a glycolate solution in ethylene glycol. Examples of such catalysts are found in U.S. Pat. No. 2,578,660, U.S. Pat. No. 2,647,885 and U.S. Pat. No. 2,789,772, which are incorporated herein by reference.

The diacid components in the polyesters to which this invention pertains are suitably alkyl dicarboxylic acids which contain from 4 to 36 carbon atoms, diesters of alkyl dicarboxylic acids which contain from 6 to 38 carbon atoms, aryl dicarboxylic acids which contain from 8 to 20 carbon atoms, diesters of aryl dicarboxylic acids which contain from 10 to 22 carbon atoms, alkyl substituted aryl dicarboxylic acids which contain from 9 to 22 carbon atoms, or diesters of alkyl substituted aryl dicarboxylic acids which contain from 11 to 22 carbon atoms. The preferred alkyl dicarboxylic acids contain from 4 to 12 carbon atoms. Some representative examples of such alkyl dicarboxylic acids include glutaric acid, adipic acid, pimelic acid and the like. The preferred diesters of alkyl dicarboxylic acids contain from 6 to 12 carbon atoms. A representative example of such a diester of an alkyl dicarboxylic acid is azelaic acid. The preferred aryl dicarboxylic acids contain from 8 to 16 carbon atoms. Some representative examples of aryl dicarboxylic acids are terephthalic acid, isophthalic acid and orthophthalic acid. The preferred diesters of aryl dicarboxylic acids contain from 10 to 18 carbon atoms. Some representative examples of diesters are aryl dicarboxylic acids, including diethyl terephthalate, diethyl isophthalate, diethyl orthophthalate, dimethyl naphthalate, diethyl naphthalate and the like. The preferred alkyl substituted aryl dicarboxylic acids contain from 9 to 16 carbon atoms and the preferred diesters of alkyl substituted aryl dicarboxylic acids contain from 11 to 15 carbon atoms.

Dihydroxy esters of dicarboxylic acids used in the processes described herein are monomeric compounds that can polymerize to a polymer. Examples of such compounds are bis(2-hydroxyethyl) terephthalate, bis(4-hydroxybutyl) terephthalate, bis(2-hydroxyethyl) naphthalenedioate, bis(2-hydroxyethyl) isophthalate, bis[2-(2-hydroxyethoxy)ethyl] terephthalate, bis[2-(2-hydroxyethoxy)ethyl]isophthalate, bis[(4-hydroxymethylcyclohexyl)methyl] terephthalate, bis[(4-hydroxymethylcyclohexyl)methyl] isophthalate, and a combination of bis(4-hydroxybutyl) terephthalate and their oligomers. Mixtures of these monomers and oligomers may also be used.

The diol component for polyesters used in the invention herein is normally comprised of glycols containing from 2 to 12 carbons atoms, glycol ethers containing from 4 to 12 carbon atoms and polyether glycols having the structural formula HO—$(AO)_n$H, wherein A is an alkylene group containing from 2 to 6 carbon atoms and wherein n is an integer from 2 to 400. Generally, such polyether glycols will have a molecular weight of about 400 to 4000.

Preferred glycols normally contain from 2 to 8 carbon atoms with preferred glycol ethers containing from 4 to 8 carbon atoms. Some representative examples of glycols that can be utilized as the diol component include ethylene glycol, 1,3-propylene glycol, 1,2-propylene glycol, 2,2-diethyl-1,3-propanediol, 2,2-dimethyl-1,3-propane diol, 2-ethyl-2-butyl-1,3-propane diol, 2-ethyl-2-isobutyl-1,3-propane diol, 1,3-butane diol, 1,4-butane diol, 1,5-pentane diol, 1,6-hexane diol, 2,2,4-trimethyl-1,6-hexane diol, 1,3-cyclohexane dimethanol, 1,4-cyclohexane dimethanol, 2,2,4,4-tetramethyl-1,3-cyclobutane diol, and the like. Some representative examples are polyether glycol (Polymeg®) and polyethylene glycol (Carbowax®).

Prepolymers of polyester copolymers can also be formed by the process of this invention. Specifically, polyesters may be modified with up to 10% by weight of a comonomer, preferably less than 5% by weight. Comonomers can include diethylene glycol (DEG), triethylene glycol, 1,4-cyclohexane dimethanol, isophthalic acid (IPA), 2,6- naphthalene dicarboxylic acid, adipic acid and mixtures thereof. Preferred comonomers for poly(ethylene terephthalate) include 0–5% by weight IPA and 0.8–3% by weight DEG.

By a "polymerizable oligomer" is meant any oligomeric material which can polymerize to a polyester. This oligomer may contain low molecular weight polyester, and varying amounts of monomer. For example, the reaction of dimethyl terephthalate or terephthalic acid with ethylene glycol, when carried out to remove methyl ester or carboxylic groups usually yields a mixture of bis(2-hydroxyethyl) terephthalate, low molecular weight polymers (oligomers) of bis(2-hydroxyethyl) terephthalate and oligomers of mono (2-hydroxyethyl) terephthalate (which contains carboxyl groups). This type of material is referred to herein as "polymerizable oligomer".

Polyesters produced by the process include, but are not limited to, poly(ethylene terephthalate), poly(1,3 propylene terephthalate), poly(1,4-butylene terephthalate), poly (ethylene naphthalenedioate), poly(ethylene isophthalate), poly(3-oxa-1,5-pentadiyl terephthalate), poly(3-oxa-1,5-pentadiyl isophthalate), poly[1,4-bis(oxymethyl)cyclohexyl terephthalate] and poly[1,4-bis(oxymethyl)cyclohexyl isophthalate]. Poly(ethylene terephthalate) is an especially important commercial product.

The oligomer produced in the present process can be used to make pellets for later use as feedstock to a polymerization process for making high molecular weight polyesters. The present oligomers are especially useful as part of an overall process for solid-state polymerization. See for example, cocurrently pending commonly assigned applications Ser. No. 08/375,873 Ser. No. 07/852,461 and Ser. No. 08/376,599 all incorporated by reference in their entirety.

EXAMPLES

Below is a description of the ranges of experimental variables carried out in the below examples. These ranges are merely exemplary of some embodiments of the invention and are not meant to be all inclusive or limiting.

Polymer temperature ranged in our examples from 271° 289° C. The range suitable for this invention is about 200° to about 400° C., preferably about 260° C. to about 320° C., assuming the lower limit is above the melting point of the oligomer in the reaction process.

The ethylene glycol/terephthalic acid mole ratio ranged in our examples from 1.13:1 to 1.3:1. The range suitable for the invention is about 1.08:1 to about 1.3:1.

Catalyst added (as ppm Sb metal) 35 to 275 ppm. Oligomer as received contained 35 ppm Sb. A suitable range for this invention is about 0 to about 300 ppm Sb.

An example of an alternate catalyst is titanium (IV) isopropoxide (added as 10 ppm titanium) in ethylene glycol. A suitable range for this invention is about 0 to about 10 ppm.

In examples 1 to 9, the pressure in the first stage of the reactor was 57 to 273 psig, and in example 10, the pressure was 41 psig. A suitable range for this invention is about 20 to 500 psig. Oligomer throughput was 0.75 to 3.0 lb/hr. Nitrogen flow rates in our examples ranged from 0.25 to 1.7 lbs $N_2$ per lb oligomer fed. Flow rates of less than 2 lbs inert gas per lb oligomer are suitable for this invention.

Pressure in the second stage of the reactor in our examples was atmospheric pressure. A suitable range of pressure in the second stage of the reaction is from about atmospheric pressure to about 25 psig. The pressure in the second stage of the reaction is reduced to a value which maintains the partial pressure of the by-products at less than the equilibrium pressure of the by-products with the prepolymer melt exiting the second stage of the reactor. For polyethylene terephthalate, a range of about 2 mm Hg to about 100 mm Hg is suitable.

A suitable residence time of the reaction mixture in the first stage is from about 1 to 60 minutes, preferably 1 to 5 minutes. A suitable residence time of the reaction mixture in the second stage is from about 1 to 60 minutes, preferably about 5 to 60 minutes. Such residence times will, however, depend on the desired product properties and economic efficiencies.

In the examples, poly(ethylene terephthalate), PET, prepolymer samples with intrinsic viscosity (IV) from 0.137 dl/gm to 0.304 dl/gm (corresponding to DPs of 8.4 to 27.1), as measured in 50/50 trifluoroacetic acid/methylene chloride, were prepared under various operating conditions in the pipeline reactor. The prepolymer may be further processed, by melt-phase polymerization or solid-state polymerization, to form polyesters with commercially useful IVs for fibers, including garments, tire cord, films, bottles, molding resins, etc.

GENERAL PROCEDURE

The feed to the pipeline reactor was terephthalic acid-based poly(ethylene terephthalate) oligomer with an intrinsic viscosity (IV) of 0.12 dl/gm and carboxyl ends of 659 Eq/$10^6$ gms. The oligomer was prepared by melt-phase esterification of terephthalic acid and ethylene glycol. The oligomer was solidified and ground prior to feeding to the pipeline process. The oligomer feed was melted in a Werner & Pfleiderer twin-screw extruder and metered into the pipeline reactor as described above using a Zenith gear pump. The oligomer feed contained 35 ppm antimony trioxide, measured as antimony metal. Ethylene glycol, containing a prescribed amount of catalyst solution (Antimony glycolate, S-24 from Elf Atochem), was injected into the pipeline using a syringe pump manufactured by either Ruska Instrument Corporation of Houston, Tex. or Isco, Inc. of Lincoln, Nebr.

The oligomer melt and ethylene glycol were passed through a Kenics static mixer section. The ethylene glycol and oligomer were allowed to react in the first stage of the pipeline reactor to incorporate the glycol into the oligomer. The first stage reactor section consisted of 10 feet of ⅜" OD coiled stainless steel tubing. Nitrogen was injected into the pipeline at a prescribed rate to reduce the partial pressure of water and glycol above the melt and drive the polymerization to the desired molecular weight through the pipeline flasher section. The nitrogen and melt were passed to the second stage through Koch and Kenics static mixers. The degree of polymerization of the finished product was controlled by varying the nitrogen flow rate. The flasher consisted of 25 feet of ½" OD coiled stainless steel tubing. The mixture of nitrogen and melt were passed through a letdown valve prior to the flasher section. The product was collected and quenched in a beaker at the exit from the pipeline.

EXAMPLE 1

Oligomer was metered at 1.0 lb/hr into the pipeline reactor. The oil bath temperature was held at 280° C. Ethylene glycol containing 1% antimony glycolate was injected at a rate of 0.0625 lb/hr, providing a mole ratio of 1.21 moles ethylene glycol/mole terephthalic acid in feed. No nitrogen was added. The pressure in the reactor section was 222 psig. The sample was collected immediately after the polyester exited the reactor section. The degree of polymerization, determined by gel permeation chromatography (GPC) was 5.04 units. The carboxyl ends, determined by titration, were 419 Eq/$10^6$ gms. This is a comparison example to show the effect of a one stage polymerization process without the use of a subsequent pressure reduction section. This shows the reduction in carboxyl ends and the degree of polymerization resulting from addition of the supplemental glucol.

EXAMPLE 2

Oligomer was metered at 0.75 lb/hr into the pipeline reactor. The oil bath temperature was held at 280° C. Ethylene glycol containing 1% antimony glycolate was injected at a rate of 0.047 lb/hr, providing a mole ratio of 1.21 moles ethylene glycol/mole terephthalic acid in feed. Nitrogen was added at a rate of 2.538 lb/hr. The pressure in the reactor section was 210 psig. The product obtained had an average IV of 0.286 dl/gm and an average of 69 Eq/$10^6$ gms carboxyl ends.

EXAMPLE 3

Oligomer was metered at 1.0 lb/hr into the pipeline reactor. The oil bath temperature was held at 280° C. Ethylene glycol containing 1% antimony glycolate was injected at a rate of 0.0625 lb/hr, providing a mole ratio of 1.21 moles ethylene glycol/mole terephthalic acid in feed. Nitrogen was added at a rate of 1.993 lb/hr. The pressure in the reactor section was 130 psig. The product obtained had an average IV of 0.256 dl/gm and an average of 61 Eq/$10^6$ gms carboxyl ends.

EXAMPLE 4

Oligomer was metered at 3.0 lb/hr into the pipeline reactor. The oil bath temperature was held at 280° C. Ethylene glycol containing 1% antimony glycolate was injected at a rate of 0.1875 lb/hr, providing a mole ratio of 1.21 moles ethylene glycol/mole terephthalic acid in feed. Nitrogen was added at a rate of 2.797 lb/hr. The pressure in the reactor section was 220 psig. The product obtained had an average IV of 0.193 dl/gm and an average of 318 Eq/$10^6$ gms carboxyl ends.

EXAMPLE 5

Oligomer was metered at 3.0 lb/hr into the pipeline reactor. The oil bath temperature was held at 280° C. Ethylene glycol containing 1% antimony glycolate was injected at a rate of 0.1875 lb/hr, providing a mole ratio of 1.21 moles ethylene glycol/mole terephthalic acid in feed. Nitrogen was added at a rate of 1.138 lb/hr. The pressure in the reactor section was 180 psig. The product obtained had an average IV of 0.186 dl/gm and an average of 284 Eq/$10^6$ gms carboxyl ends.

EXAMPLE 6

Oligomer was metered at 1.0 lb/hr into the pipeline reactor. The oil bath temperature was held at 280° C. Ethylene glycol containing 0.75% antimony glycolate was injected at a rate of 0.0938 lb/hr, providing a mole ratio of 1.31 moles ethylene glycol/mole terephthalic acid in feed. Nitrogen was added at a rate of 2.227 lb/hr. The pressure in the reactor section was 100 psig. The product obtained had an average IV of 0.208 dl/gm and an average of 72 Eq/$10^6$ gms carboxyl ends.

EXAMPLE 7

Oligomer was metered at 1.0 lb/hr into the pipeline reactor. The oil bath temperature was held at 280° C. Ethylene glycol containing no additional catalyst was injected at a rate of 0.0781 lb/hr, providing a mole ratio of 1.26 moles ethylene glycol/mole terephthalic acid in feed. Nitrogen was added at a rate of 1.760 lb/hr. The pressure in the reactor section was 220 psig. The product obtained had an average IV of 0.189 dl/gm and an average of 84 Eq/$10^6$ gms carboxyl ends.

EXAMPLE 8

Oligomer was metered at 1.0 lb/hr into the pipeline reactor. The oil bath temperature was held at 290° C. Ethylene glycol containing 1% antimony glycolate was injected at a rate of 0.0625 lb/hr, providing a mole ratio of 1.21 moles ethylene glycol/mole terephthalic acid in feed. Nitrogen was added at rate of 2.278 lb/hr. The pressure in the reactor section was 190 psig. The product obtained had an average IV of 0.247 dl/gm and an average of 139 Eq/$10^6$ gms carboxyl ends.

EXAMPLE 9

Oligomer was metered at 3.0 lb/hr into the pipeline reactor. The oil bath temperature was held at 280° C. Ethylene glycol containing 1% antimony glycolate was injected at a rate of 0.0163 lb/hr, providing a mole ratio of 1.13 moles ethylene glycol/mole terephthalic acid in feed. Nitrogen was added at a rate of 2.123 lb/hr. The pressure in the reactor section was 235 psig. The product obtained had an average IV of 0.172 dl/gm and an average of 176 Eq/$10^6$ gms carboxyl ends.

EXAMPLE 10

Oligomer was metered at 0.9 lb/hr into the pipeline reactor. The oil bath temperature was held at 280° C. Ethylene glycol was injected at a rate of 0.0221 lb/hr, providing a mole ratio of 1.08 moles ethylene glycol/mole tereptnalic acid in feed. Nitrogen was added at a rate of 0.991 lb/hr. The pressure in the reactor section was 41 psig. The product obtained had an average IV of 0.22 dl/g and an average of 111 Eq/$10^6$ g carboxyl ends.

What is claimed is:

1. A process for preparing a prepolymer with a reduced carboxyl to hydroxyl ends balance, the process comprising:
    (a) a first stage of the process, in a pipeline reactor having at least two stages, contacting a monomeric polyol with a polyester oligomer feed material, in melt form, at a pressure which is at least about 20 psig, wherein the monomeric polyol to acid ratio of the polyester oligomer feed is between about 1.01:1 to 1.5:1, and wherein the monomeric polyol has at least two hydroxy functionalities and the polyester oligomer feed material has a degree of polymerization (DP) of 2 to 10 and a carboxyl to hydroxy ratio of 1:1 to 1:0.25; and
    (b) in a second stage of the process, in a pipeline reactor, removing volatile reaction by-products, including water and excess monomeric polyol, from the melt, wherein the second stage is at a reduced pressure compared to the first stage and wherein an inert gas is introduced into the second stage, either with the reaction mixture or in a separate stream, thereby increasing the molecular weight of the product exiting the first stage and producing, as a product of the second stage, a prepolymer having a degree of polymerization of 2 to 40 and a carboxyl to hydroxyl ends balance between about 1:2 to 1:8.

2. The process of claim 1, comprising a diol to acid ratio is about 1.1:1 to about 1.5:1.

3. The process of claim 1 or 2, wherein the pressure in the first stage is above the vapor pressure of the polyol and the pressure in the second stage is reduced to a value which maintains the partial pressure of the by-products at less than the equilibrium pressure of the by-products with the melt of the prepolymer exiting the second stage of the reactor.

4. The process of claim 1 or 3, wherein the pressure in the second stage is reduced by the injection of an inert gas near the end of the first stage of the process.

5. The process of claim 1 or 3, wherein a vacuum is applied to the second stage.

6. The process of claim 4, wherein the inert gas is nitrogen.

7. The process of claim 1, wherein the prepolymer exiting the second stage of the reactor has a degree of polymerization of between about 10 and 35.

8. The process of claim 1, further comprising an effective amount of catalyst in the process, which catalyst is selected from the group consisting of compounds of antimony, germanium and titanium, and mixtures thereof.

9. The process of claim 1, wherein the acid is terephthalic acid and the glycol is ethylene glycol.

10. The process of claim 1, wherein the oligomer feed material comprises a dihydroxy ester of a bifunctional carboxylic acid selected from the group consisting of bis(2-hydroxyethyl) terephthalate, bis(4-hydroxybutyl) terephthalate, bis(2-hydroxyethyl)naphthalenedioate, bis(2-hydroxyethyl) isophthalate, bis[2-(2-hydroxyethoxy)ethyl] terephthalate, bis[2-(2-hydroxyethoxy)ethyl] isophthalate, bis[(4-hydroxymethylcyclohexyl)methyl] terephthalate, bis[(4-hydroxymethylcyclohexyl)methyl] isophthalate, and a combination of bis(4-hydroxybutyl) terephthalate, and mixtures thereof.

11. The process of claim 9, wherein the temperature is in the range extending from just above the melting point of the oligomer to 400° C.

12. The process of claim 9, wherein the residence time of the first stage is from about 1 to about 60 minutes and the residence time of the second stage is from about 1 to about 60 minutes.

13. A process for preparing a prepolymer with a reduced carboxyl to hydroxyl ends balance, the process comprising:

(a) in a first stage of the process, in a pipeline reactor having at least two stages, contacting a monomeric polyol with a polyester oligomer feed material, in melt form, at a temperature of about 200° C. to 400° C., at a pressure which is between about 20–300 psig, wherein the monomeric polyol to acid ratio of the polyester oligomer feed is between about 1.01:1 to 1.5:1, the monomeric polyol has at least two hydroxy functionalities, and the polyester oligomer has a degree of polymerization (DP) of 2 to 10 and the ratio of carboxyl to hydroxy ends is 1:1 to 1:0.25; and (b) in a second stage of the process, in a pipeline reactor, removing volatile reaction by-products, including water and excess monomeric polyol, from the melt, wherein the second stage is at a reduced pressure compared to the first stage, which reduced pressure maintains the partial pressure of the by-products at less than the equilibrium pressure of the by-products with the melt of the prepolymer exiting the second stage of the reactor and wherein an inert gas is introduced into the second stage, either with the reaction mixture or in a separate stream, thereby increasing the molecular weight of the product exiting the first stage and producing, as a product of the second stage, a prepolymer having a degree of polymerization of 2 to 40 and the ratio of carboxyl to hydroxy ends is between about 1:2 to 1:8.

14. The process of claim 13, wherein the oligomer feed material comprises a dihydroxyester of a dicarboxylic acid selected from the group consisting of bis(2-hydroxyethyl) terephthalate, bis(4-hydroxybutyl) terephthalate, bis(2-hydroxyethyl)naphthalenedioate, bis(2-hydroxyethyl) isophthalate, bis[2-(2-hydroxyethoxy)ethyl] terephthalate, bis[2-(2-hydroxyethoxy)ethyl] isophthalate, bis[(4-hydroxymethylcyclohexyl)methyl] terephthalate, bis[(4-hydroxymethylcyclohexyl)methyl] isophthalate, and a combination of bis(4-hydroxybutyl) terephthalate, and mixtures thereof.

15. The process in claim 13, wherein the polyester produced is poly(ethylene terephthalate).

16. The process in claim 13, wherein the polyester produced is poly(propylene terephthalate).

17. The process in claim 13, wherein the polyester produced is poly(butylene terephthlate).

18. The process in claim 13, wherein the polyester produced is poly(ethylene naphthalate).

19. A process for preparing a prepolymer of poly(ethylene terephthalate) with a reduced carboxyl to hydroxyl ends balance, the process comprising:

(a) in a first stage of the process, in a pipeline reactor having at least two stages, contacting glycol with a poly(ethylene terephthalate) oligomer feed material, in melt form, at a pressure at least 20 psig, wherein the glycol to acid ratio of the poly(ethylene terephthalate) oligomer feed is between about 1.01:1 to 1.5:1, and wherein the poly(ethylene terephthalate) oligomer has a degree of polymerization (DP) of 2 to 10 and a carboxyl to hydroxy ratio of 1:1 to 1:0.25; and (b) in a second stage of the process, in a pipeline reactor, removing volatile reaction by-products, including water and excess glycol, from the melt, wherein the second stage is at a reduced pressure compared to the first stage and wherein an inert gas is introduced into the second stage, either with the reaction mixture or in a separate stream, thereby increasing the molecular weight of the product exiting the first stage and producing, as a product of the second stage, a poly (ethylene terephthalate) prepolymer having a degree of polymerization of 2 to 40 and a carboxyl to hydroxy ends balance between about 1:2 to 1:8.

* * * * *